(12) United States Patent
Kannel

(10) Patent No.: US 9,429,511 B1
(45) Date of Patent: Aug. 30, 2016

(54) METHOD OF DETECTING A LUBRICATION STATUS BETWEEN A DECK AND A BELT OF A TREADMILL

(71) Applicant: Mark Kannel, Oconomowoc, WI (US)

(72) Inventor: Mark Kannel, Oconomowoc, WI (US)

(73) Assignee: Johnson Health Tech Co., Ltd., Taichung (TW)

( * ) Notice: Subject to any disclaimer, the term of this patent is extended or adjusted under 35 U.S.C. 154(b) by 34 days.

(21) Appl. No.: 14/637,368

(22) Filed: Mar. 3, 2015

(51) Int. Cl.
*G01N 19/02* (2006.01)
*A63B 22/02* (2006.01)

(52) U.S. Cl.
CPC ........... *G01N 19/02* (2013.01); *A63B 22/0235* (2013.01)

(58) Field of Classification Search
None
See application file for complete search history.

(56) References Cited

U.S. PATENT DOCUMENTS 5,433,679 A * 7/1995 Szymczak .............. A63B 22/02
184/15.3

\* cited by examiner

*Primary Examiner* — Robert R Raevis

(57) ABSTRACT

The present invention relates to a method of detecting a lubrication status between a deck and a belt of a treadmill. The method includes: starting a lubrication detecting procedure of the treadmill by a user, making the belt driving system drive the belt to run for a period of time without the user on the belt of the treadmill, having the user walk on the belt of the treadmill for a period of time at a level state, having the user walk on the belt of the treadmill for a period of time at a predetermined angle. Thereafter, a central control unit of the treadmill calculates a friction coefficient between the belt and the deck of the treadmill according to measuring results of the procedures, and generating a suggestion of maintenance according to a level of the friction coefficient.

19 Claims, 3 Drawing Sheets

METHOD OF DETECTING A LUBRICATION STATUS BETWEEN A DECK AND A BELT OF A TREADMILL

BACKGROUND

1. Field of the Invention

The present disclosure relates to a detecting method. More particularly, the present disclosure relates to a method of detecting a lubrication status between a deck and a belt of a treadmill.

2. Description of the Related Art

Currently, a typical electric treadmill has a platform which comprises a frame, a rectangular deck sustained on the frame, two parallel rollers pivotally mounted on the frame and disposed at the front end and the rear end of the deck, an endless belt mounted around the front roller and the rear roller and across a top and a bottom of the deck, and a motor for driving the front roller. In a normal driving mode, when the belt is driven by the roller to rotate forwardly, the portion of the belt on the top of the deck is circularly rotated from the front to the rear, so that an exerciser could walk or run on the belt in place. Namely, when the exerciser steps on the belt, the underneath deck would support the weight of the exerciser; meanwhile, the belt would also sustain the feet of the exercise flatting on the top of the deck to slide backward until the feet of the exercise raises to step forward again.

In the above configuration, the top surface of the deck and the inner surface of the belt are generally applied the lubrication action, e.g. waxing or oiling so as to have the stepping portion of the belt be able to slide over the deck smoothly. However, since the interface between the deck and the belt may gradually appear chips, dust, etc. Besides, the waxing layer and the lubricating oil at the top surface of the deck and the inner surface of the belt would also gradually wear and disappear. In other words, the lubrication status between the belt and the deck would become progressively worse over time. Therefore, the treadmill owner or treadmill maintenance personnel need to clean the top surface of the deck and the inner surface of the belt regularly, and/or add the lubricating oil or the like to the top surface of the deck and the inner surface of the belt. Otherwise, when the coefficient of friction between the belt and the deck is too large, the power consumption of the treadmill will increase, the motor may overheat easily, the life time of the belt and the deck will be shortened, more importantly, the running or walking movement of exerciser will become not smooth, and the belt may even get stuck to cause danger. In contrary, if the lubrication status between the belt and the deck is still normal, but inexperienced maintenance personnel still add lubricating oil to the interface of the deck and the belt, it may cause the inner surface of the belt over lubrication so that the slip phenomenon between the belt and the roller may occur easily, and not only reduces the transmission efficiency, but also affects the exercising of the exerciser so that it is dangerous.

Therefore, to correctly determine the lubrication status of the belt and the deck and to clean and lubricate appropriately, are maintenance priorities of ensuring the normal operation of the treadmill. However, because the abrasion and the consumption rate of the lubricating substance on the top surface of the deck and the inner surface of the belt will be varied from the actually running mileage for user use, exercising modes such as speed, grade, the user's weight, seasons and climate, the composition of the lubricating substance, etc., to arrange every few months or a fixed number of cumulative hours to perform one operation of cleaning and lubricating, may not be the most appropriate time for maintenance. Certainly, if the user doesn't maintain until the movement of the belt is not smooth, it is usually too late since the inner surface of the belt and the top surface of the deck may wear seriously and the belt must be replaced, renewed or the deck must be turned for being used normally.

In order to accurately detect the lubrication status of the belt and the deck, the treadmill maintenance personnel may use a professional apparatus through a set of manual procedure to calculate the coefficient of friction. However, the professional apparatus is very expansive, and the calculation result is influenced by many operating conditions such that the accuracy needs to rely on the detecting technique of the personnel.

One existing technique is achieved by mans of monitoring the current consumption of the treadmill or motor to simply determine the lubrication status between the belt and the deck. For example, the product on the market is called "Treadmill Saver®", which is connected between an indoor power socket and a power input port of the tested treadmill. The device not only transfers power to the treadmill, but also continuously monitors the current consumption of the whole treadmill. According to the high/low level of the average current consumption, the device will show different lights to notice the corresponding messages. Specifically, from lower power consumption to higher power consumption, the device will represent green light for "normal use/routine maintenance", yellow light for "should be checked" and red light for "should repair"; the principle is, since the treadmill power consumption is mainly on the use of the motor to drive the belt, in theory if other variables is ignored, when the friction force between the belt and the deck becomes larger/smaller, the current consumption of the motor (corresponding to the output torque of the motor) will be higher/lower. Therefore, when the average current consumption of the treadmill in a period (e.g. the actual use of 10 hours) exceeds one preset warning value, it usually presents that the friction coefficient between the belt and the deck is too high and the treadmill should be maintained or repaired. Base on the same principle, the circuit system of the treadmill may be designed to monitor the current consumption of the motor directly, and to display the relevant information on the console of the treadmill. However, simply base on the average current consumption of the treadmill or the motor in the period to determine the lubrication status between the belt and the deck, it would ignore a number of factors that may affect the current level within that period, e.g. the weight of the exerciser, the speed of the belt, the grade of the platform, other power consumption of the treadmill. Thus, the accuracy and the reliability of the judgment result are not enough to correctly calculate the coefficient of friction between the belt and the deck.

According to the basic physics formula, the friction force of two contacting objects is equal to the relative force of the two objects perpendicular to the friction plane multiplied by the coefficient of friction. Applying the basic physics formula to the treadmill, when someone steps on the level platform and the belt is driven by the motor to slide over the top surface of the deck, the friction force between the belt and the deck is equal to the gravity force of the user multiplied by the friction coefficient between the belt and the deck. Thus, if knowing the output torque from the motor driving the belt (corresponding with the friction force) and the user weight (corresponding to said gravity force), in combination with other data (e.g. motor torque and drive ratio as no load is on the belt), the coefficient of friction between the belt and the deck might be appropriately calculated in theory. Namely, depending on the requirement of detecting the lubrication status between the belt and the deck, a set of detecting method may be designed, e.g. having the treadmill indicate an inspector to walk slowly on the belt at a low speed and measuring the motor torque or motor current during the procedure, and requiring the inspector to enter the weight value so as to calculate the coefficient of friction. However, most people are just roughly aware of their weight; besides, the daily body weight or total weight may be changed. Therefore, in the aforementioned methods, the difference between the weight entered by the inspector and the actual load on the belt will make the calculation result appear an error to influence the measuring accuracy and reliability. Of course, the inspector may use additional body weight meter to confirm the actual weight at first, but it will make the detecting procedure bothersome and incoherent; moreover, the body weight meter may be not accurate and available.

The present invention has arisen to mitigate and/or obviate the disadvantages of the conventional method. Further benefits and advantages of the present invention will become apparent after a careful reading of the detailed description with appropriate reference to the accompanying drawings.

SUMMARY

The present invention is directed to a detecting method that meets the needs. The object of the present invention provides a method for detecting a lubrication status between a belt and a deck of a treadmill to obtain a testing result with good reliability by a simple apparatus and procedures.

According to one aspect of the present invention, the treadmill includes a belt driving system and a central control unit. The belt driving system has a motor, a driving circuit for driving the motor and a transmission mechanism for transmitting a power from the motor to the belt. The central control unit is provided to control and monitor an operation of the belt driving system. The method comprising: starting a detecting procedure of the treadmill by a user; making the belt driving system drive the belt to run for a first period of time without the user on the belt of the treadmill; having the user walk on the belt of the treadmill for a second period of time at a first angle of the deck as the belt driven by the belt driving system; having the user walk on the belt of the treadmill for a third period of time at a second angle of the deck as the belt driven by the belt driving system; and displaying information about the lubrication status to the user. For example, the central control unit calculates the friction coefficient through above procedures, and/or generating a suggestion of maintenance according to a level of the friction coefficient.

The calculation method of the friction coefficient includes: under a situation that no load on the belt of the treadmill, the central control unit controls the belt driving system to drive the belt, and detects and records parameter proportional to driving force of the belt driving system for driving the belt, e.g. motor torque, torque of a rotating component of the transmission mechanism, motor current, motor voltage, motor power to define a first value; under another situation that the deck presents at first angle and the user walk on the belt, the central control unit detects and records parameter to define a second value; under the other situation that the deck presents at second angle and the user walk on the belt, the central control unit detects and records parameter to define a third value; and the first, second and third values are substituted into a calculation formula by the central control unit to obtain the friction coefficient.

For instance, suppose the first angle corresponds to a first grade G1(%) and the second angle corresponds to a second grade G2(%), the friction coefficient between the deck and the belt could be calculated by the following formula:

$$\text{Friction Coefficient} = \frac{(\text{second value} - \text{first value}) \times G2 - (\text{third value} - \text{first value}) \times G1}{\text{second value} - \text{third value}}$$

Further, if the first angle is level, namely G1=0%, the calculation formula could be simplified as following:

$$\text{Friction Coefficien} = \frac{\text{second value} - \text{first value}}{\text{second value} - \text{third value}} \times G2$$

The reader is advised that this summary is not meant to be exhaustive. Further features, aspects, and advantages of the present invention will become better understood with reference to the following description, accompanying drawings and appended claims.

Further benefits and advantages of the present invention will become apparent after a careful reading of the detailed description with appropriate reference to the accompanying drawings.

DETAIL DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically depicted in order to simplify the drawings.

Figure 2:
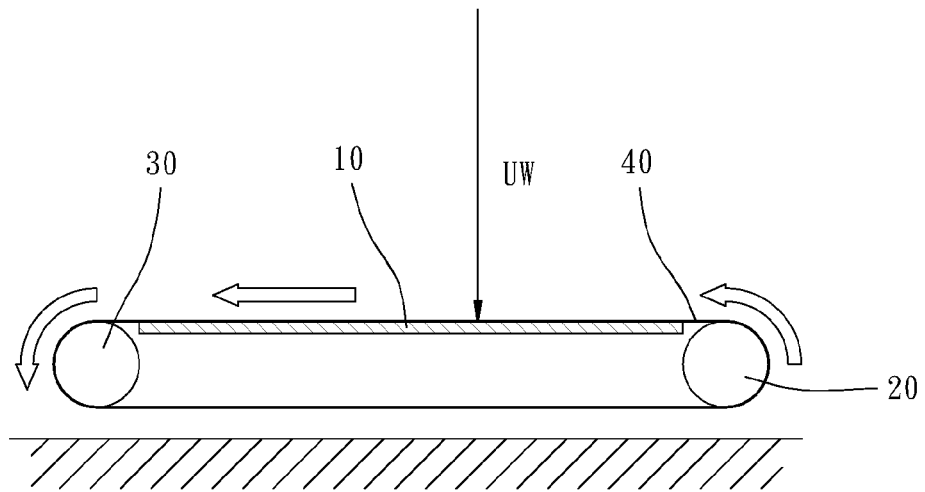
FIG. 2 illustrates an operating system that the platform of the treadmill is operated in a level state.

Accordance with a preferred embodiment of the present invention, a method of detecting a lubrication status between a belt and a deck could be applied to current motor-driven treadmills, namely one treadmill with an electric motor for driving the belt (rather than a non-electric treadmill, the belt of which is powered by a user). As shown in FIG. 2, The motor-driven treadmill, "treadmill" for short, has a platform comprising a deck 10, a front roller 20 at a front end of the deck 10, a rear roller 30 at a rear end of the deck 10 and an endless belt 40 disposed around the front roller 20 and the rear roller 30 and across a top and a bottom of the deck 10. Specially, an inner side of the belt 40 above the deck 10 is closed to a top surface of the deck 10. Generally, when no load is on the belt 40, the belt 40 does not contact with the deck 10 substantially, or is just merely in connect with the deck 10 which could be neglected. Therefore, there is almost no friction between the belt 40 and the deck 10 initially. In contrast, when the user treads on the belt 40 upon the deck 10, the friction between them is direct proportional to the body weight of the user and the friction coefficient between the belt 40 and the deck 10.

The platform of the treadmill has an electric motor (not shown) at a front end thereof for driving the front roller 20. The motor is driven by a driving circuit for controlling an operation of the motor. The driving circuit comprises a power supply circuit, a speed control circuit such as a pulse width modulation (PWM) circuit for controlling the speed of DC motors or a frequency conversion circuit for controlling the speed of AC motors, a detection or feedback circuit module, etc., so as to drive the motor and make the rotation speed of the motor retain at a predetermined speed. Generally, there are some transmission elements forming a speed reduction transmission mechanism between the motor and the front roller 20. For instance, a motor shaft is parallel to a rotating shaft of the front roller 20, and the two shafts coaxially connect a small belt pulley and a large belt pulley respectively. The two belt pulleys are looped by a transmission belt to define a primary speed reduction transmission. Moreover, an intermediate transmission shaft could be disposed between the motor shaft and the rotating shaft of the roller to define a secondary speed reduction transmission. Moreover, the motor could be mounted in the hollow front roller 20. Clearly, the motor is fixed relative to the platform and a speed reduction gear set is mounted in the front roller 20 for driving the front roller 20. The aforementioned transmission elements such as belt pulleys, the transmission shaft, the transmission belt and gears, are combined with the front roller 20 to define a transmission mechanism for transmitting a power from the motor to the belt 40. According to the normal driving mode, the motor is driven by the driving circuit to be operated forwardly to make the front roller 20 rotate reversely as shown in FIG. 2, and therefore drives the belt 40 around the two rollers 20, 30 to move forwardly as indicated by the hollow arrows in FIG. 2, such that the belt 40 upon the deck 10 moves circularly from the front end to the rear end, which provides the user with walking or running on the belt in place. Moreover, the driving circuit could also drive the motor to operate reversely, namely, the belt 40 could move reversely such that the user could walk or run backwards in place. Additionally, the motor, the driving circuit and the transmission mechanism constitute a belt driving system of the treadmill.

In the preferred embodiment of the present invention, the platform of the treadmill must be adjusted with respect to an angle of inclination to the ground, namely, grade adjustment. Nowadays, the recently commercial motor-driven treadmills generally have an electric adjusting mechanism with additional motor disposed in the front end of the platform. The adjusting mechanism could be electrically operated to control positions of its structural members so as to drive the front end of the platform rising up or descending down, therefore adjusting the inclined angle of the platform of the treadmill. Typically, the platform could be multistage adjusted and positioned between the deck 10 of level and the deck 10 of maximum grade (e.g. grade of 15%) so as to provide the user with a choice of simulated modes for running or walking on a level ground or a specific uphill slop. In addition, the treadmill could also be operated to make the front end of the platform lower than the rear end of the platform so as to provide the user with another simulated mode for exercise downhill. It should be noted that the method for adjusting the inclined angle of the platform/deck is not limited by the electric adjusting mechanism of the present invention. In other words, the manual method for adjusting the inclined angle (e.g. by means of pulling or folding front end legs of the platform) of the conventional household treadmills, which could perform the method of detecting the lubrication status of the present invention. Specifically, the platform/deck of the present invention should be adjusted in at least two different angles.

The treadmill further has a console (not shown) mounted above the front end of the platform. The console has an input interface (generally formed by a plurality of buttons) for the user keying any instructions or information, and an output interface (e.g. displays, light signals, or horns) for outputting varieties of visual and auditory information to the user. In the preferred embodiment of the present invention, in order to well guide the user (an indicator) during the detecting process and display detecting results well, the output interface includes a display device which can display text messages, e.g. a liquid crystal display (LCD), a dot matrix display, or a character display module consist of several parallel 14-/16-segment displays.

The circuit system of the treadmill has a central control unit generally defined in the console. The core of the central control unit may be a microcontroller unit (MCU) with built-in specific program, or a combination of a plurality of processors and memories. In short, the central control unit is capable of integration for processing electric signals with respect to input/output control and mechanical control of the treadmill by a predetermined manner, including accepting and processing the instructions and the information from the input interface, controlling and monitoring the operation of the belt driving system (and the electric adjusting mechanism, if any), controlling the output of the output interface, etc. The central control unit stores a special program with respect to detecting the lubrication status between the belt 40 and the deck 10, which can be executed by a predetermined operation, such as controlling, measuring, recording or calculation, sequentially or logically according to the program, and can be finished by the detecting procedure through the output interface guidelines to assist inspectors.

Figure 1:
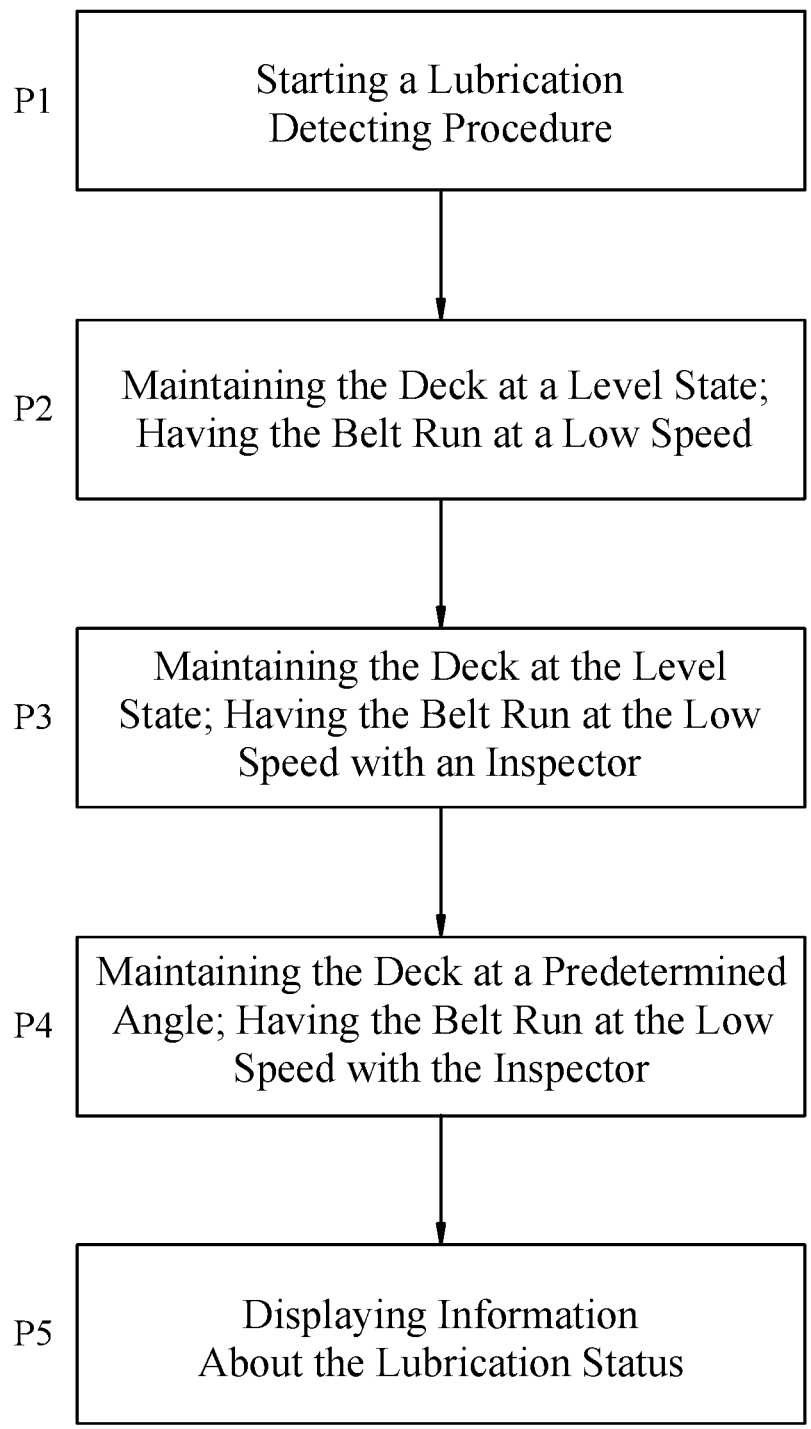
FIG. 1 is a flowchart of a method for detecting a lubrication status between a belt and a deck of a treadmill in accordance with a preferred embodiment of the present invention.

The above is the basic configuration of the motor-driven treadmill applied in the present invention. The method, the principle and the efficiency of the present invention are illustrated below. Referring to FIG. 1, the method of detecting a lubrication status between the belt 40 and the deck 10 is provided in accordance with the preferred embodiment of the present invention. The executive procedures is described as follows:

Procedure (1): First, an inspector, who wants to execute a detecting procedure for knowing the lubrication status between the belt 40 and the deck 10, e.g. treadmill maintenance personnel, treadmill owner, or user, is involved. When the inspector gives an instruction to perform the detecting procedure via the input interface of the console of the treadmill, the central control unit starts the detecting procedure in response to the above instruction, thereafter displays text messages on the display device of the output interface to the inspector, and/or generates voice prompts through a horn of the output interface to inform that the detecting procedure is begun such as "start testing procedure, please act according to the instructions". For safety considerations and operational rationality, it may be designed that the inspector should make the treadmill stop at first, and have the operating system of the console into an administration mode; or at least after sport programs end and the belt 40 stops running, the central control unit starts to provide instruction items for detecting the lubrication status on the console.

Procedure (2): If necessary, the central control unit controls the belt driving system to make the belt 40 stop running, and controls the electric adjusting mechanism to make the platform to the level position. If the angle of platform of the treadmill needs to be adjusted manually, the output interface would inform a message such as the words "Please conform treadmill platform at level state, adjust it if necessary, and press confirmation key thereafter" or the like, to instruct the inspector to manually adjust the platform to the level state, if necessary. When the central control unit confirms that the belt 40 has stopped running and the platform at the level state, the output interface informs the inspector message "Please keep the belt clean", "Press confirmation key if everything is ready", "Running belt will begin operation in N seconds" or the like, to instruct the inspector not stand on the belt 40 such that the inspector may leave the platform or stand on two sides of a support frame of the platform. After obtaining a confirmation or a notified countdown time which has been ended, the central control unit controls the belt driving system to make the belt 40 run for a predetermined period of time (e.g. 30 seconds) at an appropriate low speed. During this period, no person shall step on the belt 40 to ensure that the belt 40 is operated in no load condition.

Procedure (3): After the belt running time has been ended in the last procedure, the central control unit controls the belt driving system to make the belt 40 stop running and then informs the inspector through the output interface, such as the words "Please stand on the belt and walk slowly while the belt is operated", "Press ENTER as ready", "Running belt will begin operation in N seconds" or the like. After obtaining a confirmation or a notified countdown time has been ended, the central control unit controls the belt driving system to make the belt 40 run to a predetermined time (e.g. 30 seconds) at an appropriate low speed so as to have the inspector walk along with the running belt 40 in place, that is, the belt 40 essentially bears a constant load thereon and slides over the deck. Otherwise, if there is no safety concern, the central control unit may have the belt 40 keep running at low speed after the belt running time has been ended in the previous procedure and then informs the inspector through the output interface, such as "Please walk slowly on the belt" or the like. Afterward the central control unit controls the belt driving system to make the belt 40 run for the predetermined period of time at the appropriate low speed.

Procedure (4): If the inclined angle of the platform of the treadmill is electrically adjusted, the central control unit still has the belt run at the low speed after the belt running time has been ended in the last procedure; meanwhile, the central control unit controls the electric adjusting mechanism to drive the platform to gradually incline upward until it reaches to a predetermined angle. In the preferred embodiment of the present invention, the inclined angle of the platform is a grade value of 15% (in the treadmill art, the degree of the inclination is generally represented by grade). Further, the belt driving system is controlled to make the belt 40 run to a predetermined time such as 30 seconds at an appropriate low speed, and have the inspector walk slowly in place along with the running belt 40 which is moved circularly from the relative higher front end to the relative lower rear end, that is, the belt driving system is controlled to have the belt 40 bear a constant-weight load and slide over the deck 10 with an inclined angle. In contrast, if the inclined angle of the platform must be adjusted manually, the central control unit will make the belt driving system stop running at first after the belt running time has been ended in the last procedure, and then informs the inspector through the output interface, such as the words "Please adjust the platform to a grade of 15% and press ENTER as ready" or the like to indicate the inspector to manually adjust the platform to a specific inclination. After obtaining a confirmation, the central control system informs the inspector again as the words "Please stand on the belt and walk slowly while the belt is operated", "Press ENTER as ready", "Running belt will begin operation in N seconds" or the like. After obtaining a confirmation or a notified countdown time has been ended, the central control unit controls the belt driving system to make the belt 40 run to a predetermined time at an appropriate low speed.

Procedure (5): After the belt running time has been ended in the last procedure, the central control unit controls the belt driving system to make the belt 40 stop running, and then informs the inspector through the output interface, such as the words "The testing procedure is finished" or the like, if possible, further to control the electric adjusting mechanism to have the platform from the inclined position to the level position, and then display the testing result to the inspector through the display device, that is, the information about the lubrication status between the belt 40 and the deck 10. In this procedure, the central control unit will calculate friction coefficient between the deck 10 and the belt 40 by a predetermined calculation formula according to the average current values of the motor which are measured in the procedure (2), procedure (3) and procedure (4) as the belt runs to the predetermined time. With respect to the information about the lubrication status between the belt 40 and the deck 10, that may contain the measured friction coefficient as the belt runs to the predetermined time, and/or rating, description, suggestion, etc. in accordance with high-low level of the friction coefficient, such as the messages "Lubrication status: good(/acceptable/not satisfactory/bad)", "No need for lubrication maintenance", "Suggest for lubrication maintenance", "Suggest to change belt and deck" or the like.

In the aforementioned procedures, in addition to the messages for indicating the inspector to obey, the central control unit may also provide a variety of information for the inspector to improve the friendliness and the safety of the testing operation. For example, the specific acts might be giving a preliminary notice of the whole process and the estimation time before the testing procedure and giving tips for current stage in each procedure, before the belt starting to run noticing the operating speed and the operating time, during the process of the belt giving a notice of the remaining time, and when the belt is going to stop giving a notice of "The belt is going to stop" or "Ready to go to the next procedure" or the like. Furthermore, if the display device is a liquid crystal display (LCD) or the like, the display device could display not only text messages but also accompany images and even dynamic images to guide or notice, so that the message transmission could be direct and rapid. In contrast, the present invention may be applied to the treadmill whose console cannot display text or voice messages. For example, the output interface just has several light emitting diodes (LED) and 7-segment display for displaying numbers. Therefore, when performing the aforementioned testing procedure, the central control unit will drive the LED to light, flash or show a specific color at a specific time, so that the inspector could follow the text information marked beside said LED to know the corresponding message, such as "Procedure (4)", "The platform maintain grade of 15%; walking for 30 sec." or "Suggest for lubrication maintenance", and/or could control said 7-segment display to display the current procedure, time, friction coefficient, etc.

The calculation means of the friction coefficient and the theoretical foundation in the aforementioned procedures are illustrated below. The present invention provides a calculating method of the friction coefficient between the deck 10 and a belt 40 of the treadmill as described in the previous procedures, including following steps. In procedure (2), under the situation of no load on the belt, the central control unit controls the belt driving system to make the belt run to the predetermined time, then detects and records the average current of the motor of the belt driving system to define a first current value. In procedure (3), under the situation that the deck 10 is maintained in the level position and the belt bears the inspector thereon, the central control unit controls the belt driving system to make the belt run to the predetermined time, then detects and records the average current of the motor to define a second current value. In procedure (4), under the situation that the deck is maintained at a specific inclined angle (grade of 15%) and bears the inspector thereon, the central control unit controls the belt driving system to make the belt run to the predetermined time, then detects and records the average current of the motor to define a third current value. In the procedure (5), the central control unit substitutes the first current value, the second current value and the third current value into the following formula to calculate the coefficient of friction between the deck 10 and the belt 40:

$$\text{Friction Coefficien} = \frac{\text{second current value} - \text{first current value}}{\text{second current value} - \text{third current value}} \times 0.15 \quad (1)$$

Figure 3:
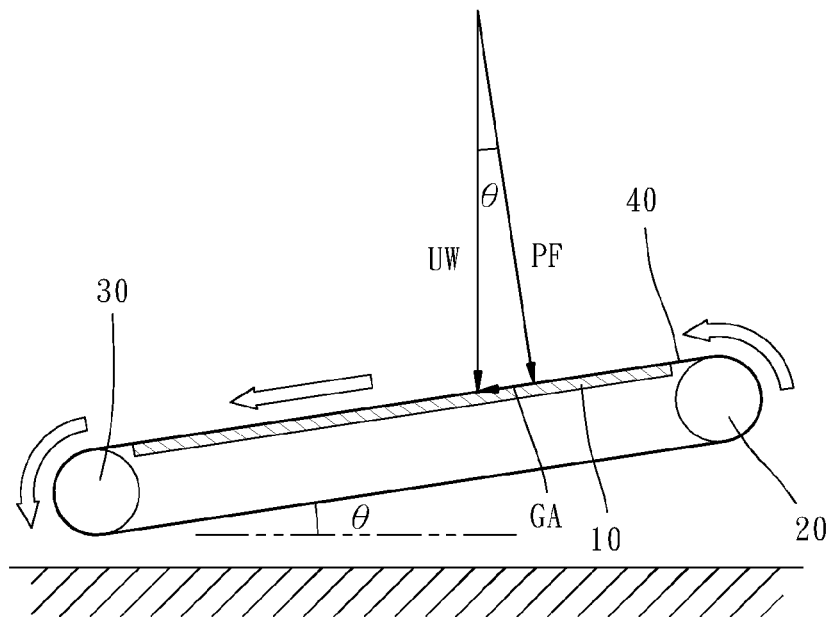
FIG. 3 illustrates another operating system that the platform of the treadmill is operated in an inclined state.

The theoretical foundation of above formula is illustrated as follows:

Referring to FIG. 2 and FIG. 3, which respectively represent the operation of the platform of the treadmill in the level state and the inclined state, the front roller 20 is driven by an output torque force of the motor to rotate counterclockwise so as to make the belt 40 around the front, rear rollers 20, 30 rotate forwardly, that is, the belt 40 on the top of the deck 10 is circularly rotated from front to rear as indicated by the hollow arrows in figures. As shown in FIG. 2 and FIG. 3, the vertical line UW (the abbreviation of User Weight) represents the corresponding gravity of the inspector's weight (called as user weight, hereafter). The length of the line segment represents the magnitude of the user weight, e.g. 100 kgf. The arrow represents the top down force of the user weight on the belt 40 upon the deck 10 so as to have the corresponding portion of the inner surface of the belt 40 flat on the top surface of the deck 10.

As shown in FIG. 2, in procedure (3), the belt 40 bears the user weight (UW) and flats on the top of the deck 10 to slide from the front to the rear. Since the user weight (UW) is perpendicular to the friction surface between the belt 40 and the deck 10, the friction between the belt 40 and the deck 10 is equal to the user weight multiplied by the friction coefficient between the belt 40 and the deck 10, that is:

$$\text{Friction}_1 = \text{User Weight} \times \text{Friction Coefficient} \quad (2)$$

Meanwhile, in previous situation, the friction is a force resisting the sliding motion of the belt 40 over the deck 10, represented as:

$$\text{Net Drag Force}_1 = \text{Friction}_1 \quad (3)$$

On the other hand, as shown in FIG. 3, in procedure (4), when the belt 40 bears the user weight (UW) and flats on the top of the inclined deck 10 to slide from the relative higher front end to the relative lower rear end, the friction between the belt 40 and the deck 10 is equal to a component force of the user weight (UW) perpendicular to the surface of the belt 40 (to call perpendicular force, PF) multiplied by the friction coefficient, namely:

$$\text{Friction}_2 = \text{User Weight} \times \cos(a\ \tan(\text{Grade}_2)) \times \text{Friction Coefficient} \quad (4)$$

In the equation (4), "Grade$_2$" is the grade value (%) in procedure (4), which is 15% in the present embodiment. (if let the inclined deck as a hypotenuse of a right triangle and let the inclined angle of the deck as an inclined angle of the right triangle, thus the "grade" of the deck is defined as the ratio of the opposite side to the adjacent side of the right triangle, namely, tangent function); "a tan(Grade$_2$)" is an inverse trigonometric to transfer the ratio of the opposite side/the adjacent side to obtain an angle value of the inclined angle θ of the deck 10 (in degrees), e.g. an elevation angle would be 8.5 degrees under the grade of 15%. In FIG. 3, as presented above the platform, a right triangle has the UW as the hypotenuse side, PF as the adjacent side and GA as the opposite side. The inclined angle θ is equal to the inclined θ of the deck 10 (the geometric principle will be described in next paragraph). According to trigonometric functions, the length of the hypotenuse side UW times "cosine of the inclined angle θ" (namely "cos(a tan(Grade$_2$))" in the equation (4) equals the length of the adjacent side PF, that is, the magnitude of the component force of the user weight (UW) is perpendicular to the surface of the belt 40. Additionally, in FIG. 3, for facilitating the drafting and the identification of charts, the line PF perpendicular to the surface of the belt 40 is painted to be concurrent with the top of the line UW, and the included angle is θ. However, in the mechanics, the perpendicular force PF and the user weight UW are both acting on the belt 40 in the same position. In other words, it is corrected to have the line PF be concurrent with the bottom of the line UW (the included angle is the same as θ), but this does not affect the correlation calculation.

Figure 4:
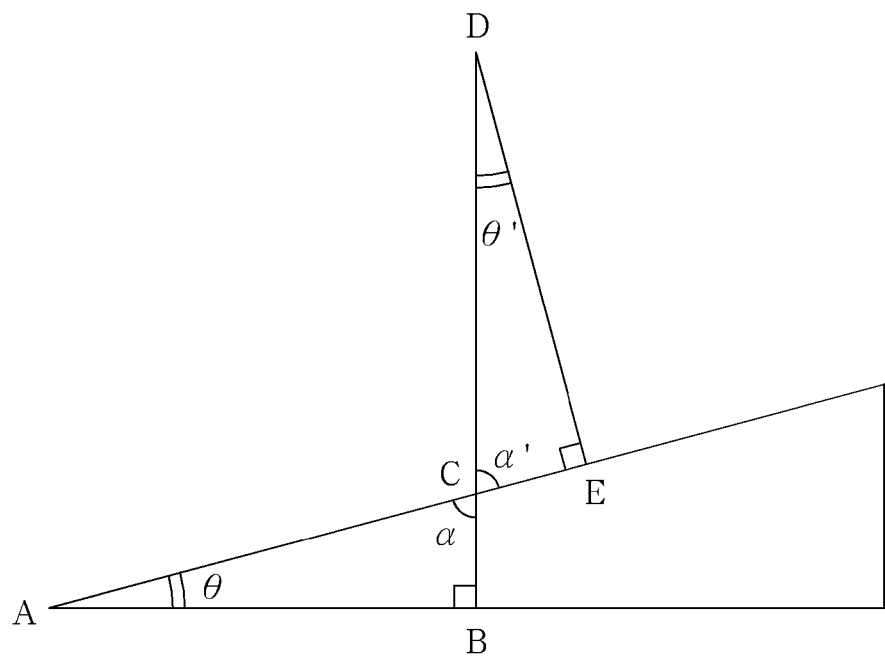
FIG. 4 presents a simple geometric principle of the two equal angles $\angle \theta$ in FIG. 3.

Referring to FIG. 3, the included angle θ between the user weight (UW) and the perpendicular force (PF) is equal to another included angle θ between the deck 10 plane and the ground level, i.e. about 8.5 degrees as mentioned above. FIG. 4 presents a simple geometric principle of the two equal angles (∠θ) in FIG. 3, as follows. In the right triangle ABC, φ0+∠α=90°; in another right triangle DEC, ∠θ'+∠α'=90°. Since ∠α'=∠α (vertical angles to each other), ∠θ'=∠θ.

Referring again to FIG. 3, the deck 10 is maintained at a predetermined inclined angle, and the belt 40 bears the user weight and flats on the top of the inclined deck 10 to slide from the relative higher front end to the relative lower rear end. Thus, a component force of the user weight with respect to the sliding direction of the belt 40 (hereafter, called Gravity Assistance, GA) will become an assistant force to facilitate the forward rotation of the belt 40. The gravity assistance (GA) is calculated by the following formula:

$$\text{Gravity Assistance}_2 = \text{User Weight} \times \sin(a\ \tan(\text{Grade}_2)) \quad (5)$$

As shown in FIG. 3, in the right triangle defined by lines UW, PF and GA, the length of the hypotenuse side UW times "sine of the inclined angle θ" (namely "sin(a tan(Grade$_2$))" in the equation (5)) equals the length of the opposite side GA, that is, the magnitude of the component force of the user weight (UW) with respect to the sliding direction of the belt 40.

Therefore, in procedure (4), the friction is a force resisting the sliding motion of the belt 40 over the deck 10. The gravity assistance (GA) is a force to facilitate the sliding motion of the belt 40 over the deck 10 from the front end to the rear end. Therefore, the summation of the drag force in regard to resist the forward sliding motion of the belt 40 over the deck 10, is equal to the friction force minus the gravity assistance (GA), that is:

Net Drag Force$_2$=Friction$_2$−Gravity Assistance$_2$ (6)

The equation (4) and the equation (5) are substituted into the equation (6), to obtain:

Net Drag Force$_2$=User Weight×cos($a$ tan(Grade$_2$))× Friction Coefficient−User Weight×sin($a$ tan (Grade$_2$)) (7)

"User Weight×cos(a tan(Grade$_2$))", namely "user weight (UW) is multiplied by cosine of the inclined angle θ" as the magnitude of the aforementioned perpendicular force (PF). In the present embodiment, since the aforementioned inclined angle θ is about 8.5 degrees and the corresponding cosine function approximate 0.989, is very close to 1, i.e. the magnitude of the perpendicular force (PF) is close to the user weight (UW), the user weight (UW) could be regarded as an approximate value of the perpendicular force (PF). For example, supposing the user weight is 100 kgf, the perpendicular force shall be calculated as 98.89 kgf; if taking an approximate value of 100 kgf, the error is only about 1%. Therefore, the equation (4) can be rewritten as below:

Friction$_2$≈User Weight×Friction Coefficient (8)

Meanwhile, "User Weight×sin(a tan(Grade$_2$))" namely "user weight (UW) multiplied by sine of the inclined angle θ" is the same as the magnitude of the aforementioned gravity assistance (GA). In the present embodiment, the aforementioned inclined angle θ is about 8.5 degrees and the corresponding sine function is approximate to the corresponding tangent function. Besides, the definition and the value of the tangent function are the same as the definition and the value of the grade (namely 0.15), so that the gravity assistance (GA) is proximate to the user weight (UW) multiplied by the grade value. For example, supposing the user weight is 100 kgf, the gravity assistance shall be calculated as 14.83 kgf; if taking an approximate value of 15 kgf, the error is also only about 1%. Therefore, the equation (5) can be rewritten as below:

Gravity Assistance$_2$≈User Weight×Grade$_2$ (9)

For supplemental instruction, in regard to the calculation method of approximating the perpendicular force (PF) and the gravity assistance (GA), the range of error will increase/decrease as the inclined angle θ increase/decrease. For instance, if the grade value of the deck 10 is 10%, corresponding to the inclined angle θ about 5.7 degrees, the error will be reduced to 0.5%; if the grade value of the deck 10 is 20%, corresponding to the inclined angle θ about 11.3 degrees, the error will be increased to 2%, but still within the acceptable range.

The equation (8) and the equation (9) are re-substituted into the equation (6), to obtain:

Net Drag Force$_2$≈(User Weight×Friction Coefficient)−(User Weight×Grade$_2$) (10-1)

Similarly, in the same system, when the deck 10 is present in a specific inclined angle (the corresponding grate is "Grade$_X$"), the net drag force in regard to resist the forward sliding motion of the belt 40 over the deck 10 could be represented as:

Net Drag Force$_X$≈(User Weight×Friction Coefficient)−(User Weight×Grade$_X$) (10-2)

The equation (10-2) not only applies to the deck 10 under the inclined state, but also applies to the deck 10 under the level state, namely, when the deck 10 is level, the grade value is 0%, that is, the gravity assistance (User Weight× Grade$_X$) is zero. Therefore, the net drag force in regard to resist the forward sliding motion of the belt 40 over the deck 10 is equal to the user weight multiplied by the friction coefficient, as the equation (2) and the equation (3).

The equations (10-1) and (10-2) is renewed, to get following equations of the user weight respectively:

$$\text{User Weight} \approx \frac{\text{Net Drag Force}_2}{\text{Friction Coefficient} - \text{Grade}_2} \quad (11\text{-}1)$$

$$\text{User Weight} \approx \frac{\text{Net Drag Force}_X}{\text{Friction Coefficient} - \text{Grade}_X} \quad (11-2)$$

Since the user weight would not change in the previous procedures, i.e. "User Weight" in the equation (11-1) and the equation (11-2) are equal, the equation (11-1) and the equation (11-2) could be merged to obtain:

$$\frac{\text{Net Drag Force}_2}{\text{Friction Coefficient} - \text{Grade}_2} \approx \frac{\text{Net Drag Force}_X}{\text{Friction Coefficient} - \text{Grade}_X} \quad (12)$$

The equation (12) is renewed to obtain the equation of the friction coefficient:

$$\text{Friction Coefficient} \approx \frac{(\text{Net Drag Force}_X \times \text{Grade}_2) - (\text{Net Drag Force}_2 \times \text{Grade}_X)}{\text{Net Drag Force}_X - \text{Net Drag Force}_2} \quad (13)$$

If the inclined angle of the deck 10 and the net drag force are substituted into the equation (13), namely, "Grade$_X$" is 0%, "Grade$_2$" is 15%, and "Net Drag Force$_X$" changes to "Net Drag Force$_1$", the equation (13) becomes as follows:

$$\text{Friction Coefficient} \approx \frac{\text{Net Drag Force}_1}{\text{Net Drag Force}_1 - \text{Net Drag Force}_2} \times 0.15 \quad (14)$$

From another point of view, in the procedure (2), since the belt 40 is not in contact with the deck 10 substantially, there is no friction between the belt 40 and the deck 10 to resist the rotating motion of the belt 40. In contrast, in the procedure (3), the belt driving system must overcome the additional friction force between the belt 40 and the deck 10 to drive the belt 40 rotating. It can be seen that the net force (namely the friction force) in the procedure (3) is equal to "(in procedure (3)) the driving force of the belt driving system for driving the belt under the situation that the deck is level and the belt bears the user weight" minus "(in procedure (2)) the driving force of the belt driving system for driving the belt under the situation that no load is on the belt", to get:

Net Drag Force$_1$=Drive Force$_1$−Drive Force$_0$ (15)

Meanwhile, in procedure (4), the net force resisting the sliding movement of the belt 40 over the inclined deck 10 is equal to "(in procedure (4)) the driving force of the belt driving system for driving the belt under the situation that the deck in present at the grade of 15% and the belt bears the user weight" minus "(in procedure (2)) the driving force of the belt driving system for driving the belt under the situation that no load is on the belt", to get:

$$\text{Net Drag Force}_2 = \text{Drive Force}_2 - \text{Drive Force}_0 \quad (16)$$

The equations (15) and (16) are substituted into the equation (14) to obtain the original formula of the friction coefficient:

$$\text{Friction Coefficient} \approx \frac{\text{Drive Force}_1 - \text{Drive Force}_0}{\text{Drive Force}_1 - \text{Drive Force}_2} \times 0.15 \quad (17-1)$$

In the equation (17-1), "Drive Force$_0$", "Drive Force$_1$" and "Drive Force$_2$" respectively represent the driving forces of the belt driving system for respectively driving the belt 40 rotating in the procedure (2), the procedure (3) and the procedure (4). Specially, the output torque of the motor of the belt driving system or the torque of any rotating component (e.g. the roller, driving shaft and gears) of the transmission mechanism has its own specific relationship to the final driving force transmitting to the belt 40. Therefore, if the driving force algebra of the equation (17-1) is replaced by the corresponding torque algebra, it will get the same ratio, namely:

$$\text{Friction Coefficient} \approx \frac{\text{Torque}_1 - \text{Torque}_0}{\text{Torque}_1 - \text{Torque}_2} \times 0.15 \quad (17-2)$$

Therefore, if mounting a torque meter on the spindle of the motor or any rotating component of the transmission mechanism, and respectively detecting and recording the average torque of the motor spindle or the rotating component in the courses of the procedure (2), the procedure (3) and the procedure (4), the three detected torque values could be substituted into the equation (17-2) in the procedure (5) to calculate the friction coefficient between the belt 40 and the deck 10.

However, the present embodiment uses a simpler method to calculate, namely, since said motor is a DC motor (note: most electric treadmills generally use DC motors), the input current of the DC motor is proportional to the output torque force (note: the simplified formula is "T=K·I"; specially, T is the total torque, K is a torque constant of the motor, and I is the total current flowing into the armature). Thus, if the torque algebra of the equation (17-2) is replaced by the corresponding current algebra, it will also get the same ratio, namely:

$$\text{Friction Coefficient} \approx \frac{\text{Current}_1 - \text{Current}_0}{\text{Current}_1 - \text{Current}_2} \times 0.15 \quad (17-3)$$

This is the origin of the equation (1), namely, in the present embodiment; the central control unit will detect and record the average current of the motor in the course of the belt 40 running to the predetermined time in the procedure (2), the procedure (3) and the procedure (4). Then, the three detected current values could be substituted into the equation (17-3) in the procedure (5) to calculate the friction coefficient between the belt 40 and the deck 10.

Similarly, if the motor is AC motor, the input voltage is proportional to the output torque, so that to substitute the average voltage values of the motor in the procedure (2), the procedure (3) and the procedure (4) into the following equation (17-4) would obtain the friction coefficient:

$$\text{Friction Coefficient} \approx \frac{\text{Voltage}_1 - \text{Voltage}_0}{\text{Voltage}_1 - \text{Voltage}_2} \times 0.15 \quad (17-4)$$

Likewise, since the power of the motor is proportional to the current and the voltage, the average power values of the motor in the procedure (2), the procedure (3) and the procedure (4) could be substituted into the following equation (17-5) to calculate the friction coefficient as follows:

$$\text{Friction Coefficient} \approx \frac{\text{Power}_1 - \text{Power}_0}{\text{Power}_1 - \text{Power}_2} \times 0.15 \quad (17-5)$$

Moreover, for the current, the voltage, the power or other electrical parameters of the motor may have a ratio or a functional relationship with that of some node in the driving circuit, the central control unit is possible to measure the specific parameter of the driving circuit instead of measuring the motor.

In short, no matter which one of, in the equations (17-2), (17-3), (17-4) and (17-5), the torque (of the motor spindle or the transmission component), the motor current, the motor voltage, the motor power, etc., or the specific parameter of the driving circuit, the value thereof is proportional to the driving force of the belt driving system.

Regarding to the equations (17-1) to (17-5), having the measured "Torque$_0$", "Current$_0$" . . . in the procedure (2) be called first value, the measured "Torque$_1$", "Current$_1$," . . . in the procedure (3) be called second value, and the measured "Torque$_2$", "Current$_2$" . . . in the procedure (4) be called third value, and having the second value minus the first value (namely numerator in the equations) defined as a first difference value, the second value minus the third value (namely denominator in the equations) defined as a second difference value, the ratio of the first difference value to the second difference value defined as a difference ratio (the fraction in the equations), the friction coefficient would be proportional to the difference ratio. Specifically, the grade of the deck 10 in the procedure (4) (i.e. 15% in the present embodiment) becomes a proportionality constant between the friction coefficient and the difference ratio, namely "0.15" in the equations. For example, if the grade of the deck 10 in the procedure (4) is 10%, the proportionality becomes 0.1; if the grade of the deck 10 in the procedure (4) is 20%, the proportionality becomes 0.2.

In the procedure (5), the central control unit can display the calculated result of the friction coefficient on the console, and/or rating, description, suggestion, etc. in accordance with high-low level of the friction coefficient, such as the messages "Lubrication status: good/acceptable/not satisfactory/bad", "No need for lubrication maintenance", "Suggest for lubrication maintenance" and "Suggest to change belt and deck" to provide the inspector with recording, assessment or taking a corresponding action.

However, in the point of the testing requirement, the inspector may not want to know the friction coefficient (definition of physics) between the belt and the deck, e.g. "how much Newton force does this belt need to get to move a person with a weight of 80 kg?" In contrast, the inspector actually just want to know "the quality or grade of the lubrication status" between the belt and the deck, namely "whether the lubrication status is good or not" or "whether the lubrication maintenance is necessary or not". From this point of view, since the grade value is constant, the object above would be achieved rely on the difference ratio. For example, supposing the relevant program is set based on the aforementioned formula "when the calculated friction coefficient is less than 0.3 "good" would be given; when the calculated friction coefficient is larger than 0.6 "bad" would be given; when the calculated friction coefficient is between 0.3 to 0.6 "acceptable" would be given", even if the difference ratio isn't multiplied by the proportionality constant "0.15" to get the friction coefficient, the corresponding judgment could be made according to the difference ratio. In other words, when the value of the difference ratio is less than 2 "good" would be given; when the value of the difference ratio is larger than 4 "bad" would be given; when the value of the difference ratio is between 2 to 4 "acceptable" would be given. Therefore, in general requirement, the messages conveyed to the inspector are actually equivalent. In other words, the detecting method of the present invention is actually provided to calculate a "lubrication index" for reflecting the lubrication status between the belt 40 and the deck 10, and then providing the inspector with the messages of the lubrication status between the belt 40 and the deck 10 according to the lubrication index. The calculating process may not involve the grade value, namely it does not calculate the friction coefficient eventually (note: the friction coefficient belongs to the lubrication index), but only calculates the difference ratio, such as:

$$\text{Lubrication Index} = \frac{\text{Current}_1 - \text{Current}_0}{\text{Current}_1 - \text{Current}_2} \quad (18)$$

Obviously, by means of collecting the first, second and third values, the central control unit can calculate the friction coefficient or the difference ratio according to the aforementioned formula. However, the achieving sequence of above three values does not affect the calculating process or result. In other words, in the detecting procedure of the present invention, it just needs to measure the values of the predetermined parameter under the three situation of "no load on the belt", "maintaining the deck at a level position and having the inspector walk on the belt" and "maintaining the deck at a predetermined inclined angle and having the same inspector walk on the belt". Specially, the three values of the achieving sequences are not limited in the detecting procedure. For example, differing from the aforementioned procedures, the present invention may direct the inspector to walk on the platform at level or inclined position to measure the second value and the third value firstly. Then, the present invention indicates the inspector to leave for the belt and let the belt idle run itself to measure the first value (note: the first value which is measured at "no load on the belt" could neglect the inclined angle of the platform), and calculates and displays the result.

Furthermore, in the procedure (3) and procedure (4) as described above, the deck is kept at the level position and the predetermined inclined position to provide the inspector walking on the belt to measure the second and third values, and to obtain the friction coefficient according to the equation (17-2) finally. However, the detecting method could also have the deck maintain at a first inclined angle in one procedure (corresponding to a first grade) to provide the inspector walking on the belt, and have the deck maintain at a second inclined angle in another procedure (corresponding to a second grade) to provide the inspector walking on the belt, and finally to calculate the friction coefficient between the belt and the deck by the following formula:

$$\text{Friction Coefficient} \approx \frac{((\text{Current}_1 - \text{Current}_0) \times \text{Grade}_2) - ((\text{Current}_2 - \text{Current}_0) \times \text{Grade}_1)}{\text{Current}_1 - \text{Current}_2} \quad (19)$$

The equation (19) is obtained by the equation (13) merged with the equation (15), and the equation (16), and by replacing the algebra appropriately. In the equation (18), "$\text{Current}_0$" also refers to the motor current without any load on the belt, and "$\text{Current}_1$" and "$\text{Current}_2$" refer to the motor currents that the deck is respectively maintained in a first inclined angle and a second inclined angle while the inspector walks on the belt. Further, "$\text{Grade}_1$" and "$\text{Grade}_2$" respectively refer to a first grade and a second grade. The equation (19) is an instance of motor current in practice. If each of current algebra is replaced by another corresponding algebra, e.g. motor torque or motor power, it would get the same ratio.

Under this arrangement, the works of measuring the parameters, calculating the lubrication index, guiding the user, displaying the detecting result, etc. are tested on the treadmill. However, part or all of above works may be achieved outside the treadmill. For example, in another embodiment of the present invention (not shown), an external device is prepared in advance. The external device is connected between an indoor power socket and a power input port of the tested treadmill when the device is used. The external device is provided with a measuring unit and a transmitting unit for sustained measuring the current consumption of the treadmill, and transmitting the instantaneous current value and the average current value through cable transmission, wireless transmission, local area network (LAN) or wide area network (WAN) directly or indirectly to a local computer device such as a desktop computer that the inspector could operate on the spot, a notebook, a tablet computer, a smart mobile phone or a built-in computer system of the treadmill. While testing, it is probable that the inspector follows indications of said computer device to have the tested treadmill be operated at states of "no load on the belt", "maintaining the deck at a first angle and having the inspector walk on the belt" and "maintaining the deck at a second inclined angle and having the inspector walk on the belt". Otherwise, the inspector himself has the tested treadmill be operated at the three states, and timely informs or notices the operation status of the treadmill to the computer device so as to have the computer device be able to correctly obtain a first value, a second value and a third value corresponding to the three operation states. Then, the current values are substituted into a predetermined formula (e.g. the former equations (17-3), (18) and (19)) to calculate and show the calculation result in corresponding messages. In this embodiment, the measuring current values from the external device not only is the motor current consumption of the belt driving system, but also contains additional power consumption e.g. treadmill console. However, the additional power consumption is generally stable and unchangeable during the testing procedure. Therefore, although "$\text{Current}_0$", $\text{Current}_1$" and $\text{Current}_2$" in the equations (17-3), (18) and (19) are substituted by the whole current consumption of the treadmill, the additional power consumption current in the denominator and the numerator of the formula will be offset, which would not affect the calculation result. In other words, using above method to calculate the lubrication index is still reliable. Accordingly, the measuring and transmitting data from the external device may be represented the current consumption of the treadmill.

In another embodiment of the present invention (not shown), an external device is provided to be connected between an indoor power socket and a power input port of the tested treadmill. It can not only measure the current consumption or power of the treadmill, but also has an operation control unit (e.g. microprocessor) and a display unit (e.g. LED signals), which could directly calculate the lubrication index and display the testing result.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of detecting a lubrication status between a deck and a belt of a treadmill, the treadmill comprising a belt driving system and a central control unit, the belt driving system having a motor, a driving circuit for driving the motor and a transmission mechanism for transmitting a power from the motor to the belt, the central control unit provided to control and monitor an operation of the belt driving system, and the method comprising:
  starting a lubrication detecting procedure of the treadmill by a user;
  performing following procedures:
    (a) making the belt driving system drive the belt to run for a first period of time without the user on the belt of the treadmill;
    (b) having the user walk on the belt of the treadmill for a second period of time at a first angle of the deck as the belt driven by the belt driving system;
    (c) having the user walk on the belt of the treadmill for a third period of time at a second angle of the deck as the belt driven by the belt driving system; and
  displaying information about the lubrication status to the user.

2. The method of claim 1, wherein the information about the lubrication status comprises a signal determined by values of a lubrication index corresponding to the lubrication status; and the lubrication index is calculated by the central control unit upon the procedures (a), (b), (c) are completed.

3. The method of claim 1, wherein the information about the lubrication status comprises a lubrication index in response to the lubrication status; and the lubrication index is calculated by the central control unit upon the procedures (a), (b), (c) are completed.

4. The method of claim 3, wherein the lubrication index is a friction coefficient between the deck and the belt.

5. The method of claim 3, wherein the central control unit detects and records parameter proportional to driving force of the belt driving system for driving the belt under the procedures (a), (b), (c) to define a first value, a second value and a third value respectively; and the first, second and third values are substituted into a calculation formula by the central control unit to obtain the lubrication index.

6. The method of claim 5, wherein the first angle is level and the second angle is an inclined angle, the calculation formula as represented below:

$$\text{Lubrication Index} = \frac{\text{second value} - \text{first value}}{\text{second value} - \text{third value}}.$$

7. The method of claim 5, wherein the first angle is level and the second angle is an inclined angle corresponding to a grade, the lubrication index being a friction coefficient between the deck and the belt, the calculation formula as represented below:

$$\text{Friction Coefficient} \approx \frac{\text{second value} - \text{first value}}{\text{second value} - \text{third value}} \times \text{grade}.$$

8. The method of claim 5, wherein the first angle is a first inclined angle corresponding to a first grade and the second angle is a second inclined angle corresponding to a second grade, the lubrication index being a friction coefficient between the deck and the belt, the calculation formula as represented below:

$$\text{Friction Coefficient} = ((\text{second value} - \text{first value}) \times \text{second grade} - (\text{third value} - \text{first value}) \times \text{first grade})/(\text{second value} - \text{third value})$$

9. The method of claim 5, wherein the parameter is average current of the motor.

10. The method of claim 5, wherein the parameter is average voltage of the motor.

11. The method of claim 5, wherein the parameter is average power of the motor.

12. The method of claim 5, wherein the parameter is average torque of the motor.

13. The method of claim 5, wherein the parameter is average torque of a rotating component of the transmission mechanism.

14. A method of detecting a lubrication status between a deck and a belt of a treadmill, the treadmill comprising a belt driving system, the belt driving system having a motor, a driving circuit for driving the motor and a transmission mechanism for transmitting a power from the motor to the belt, and the method comprising:
  arranging a measuring unit connected to the driving circuit, an operation control unit connected to the measuring unit and the display unit connected to the operation control unit;
  starting a lubrication detecting procedure of the treadmill by a user;
  performing following procedures:
    (a) making the belt driving system drive the belt to run for a first period of time without the user on the belt of the treadmill;
    (b) having the user walk on the belt of the treadmill for a second period of time at a first angle of the deck as the belt driven by the belt driving system;
    (c) having the user walk on the belt of the treadmill for a third period of time at a second angle of the deck as the belt driven by the belt driving system; and
  displaying information about the lubrication status to the user.

15. The method of claim 14, wherein the information about the lubrication status comprises a signal determined by values of a lubrication index corresponding to the lubrication status; and the lubrication index is calculated by the central control unit upon the procedures (a), (b), (c) are completed.

16. The method of claim 14, wherein the information about the lubrication status comprises a lubrication index in response to the lubrication status; and the lubrication index is calculated by the central control unit upon the procedures (a), (b), (c) are completed.

17. The method of claim 16, wherein the lubrication index is a friction coefficient between the deck and the belt.

18. The method of claim 16, wherein the central control unit detects and records parameter proportional to driving force of the belt driving system for driving the belt under the procedures (a), (b), (c) to define a first value, a second value and a third value respectively; and the first, second and third values are substituted into a calculation formula by the central control unit to obtain the lubrication index.

19. The method of claim 18, wherein the first angle is a first inclined angle corresponding to a first grade and the second angle is a second inclined angle corresponding to a second grade, the lubrication index being a friction coefficient between the deck and the belt, the calculation formula as represented below:

$$\text{Friction Coefficient} = ((\text{second value} - \text{first value}) \times \text{second grade} - (\text{third value} - \text{first value}) \times \text{first grade}) / (\text{second value} - \text{third value})$$

* * * * *